(12) United States Patent
Bala

(10) Patent No.: US 12,253,500 B2
(45) Date of Patent: Mar. 18, 2025

(54) GAS STERILIZATION PROCESS CHALLENGE DEVICE

(71) Applicant: American Sterilizer Company, Mentor, OH (US)

(72) Inventor: Harry Bala, South Barrington, IL (US)

(73) Assignee: American Sterilizer Company, Mentor, OH (US)

( * ) Notice: Subject to any disclaimer, the term of this patent is extended or adjusted under 35 U.S.C. 154(b) by 855 days.

(21) Appl. No.: 17/409,398

(22) Filed: Aug. 23, 2021

(65) Prior Publication Data

US 2023/0053793 A1   Feb. 23, 2023

(51) Int. Cl.
*G01N 31/22* (2006.01)
*A61L 9/04* (2006.01)
*A61L 9/12* (2006.01)
*A61L 101/38* (2006.01)

(52) U.S. Cl.
CPC ............. *G01N 31/226* (2013.01); *A61L 9/04* (2013.01); *A61L 9/12* (2013.01); *A61L 2101/38* (2020.08); *A61L 2209/211* (2013.01)

(58) Field of Classification Search
None
See application file for complete search history.

(56) References Cited

U.S. PATENT DOCUMENTS

| | | | |
|---|---|---|---|
| 4,914,034 A * | 4/1990 | Welsh | C12Q 1/22 435/31 |
| 7,790,105 B2 | 9/2010 | Bala | |
| 9,017,994 B2 | 4/2015 | Franciskovich et al. | |
| 2003/0162243 A1 * | 8/2003 | Foltz | G01N 31/226 435/31 |
| 2009/0028753 A1 | 1/2009 | Bala | |
| 2010/0036357 A1 * | 2/2010 | Bala | A61L 2/28 604/404 |
| 2016/0000954 A1 * | 1/2016 | Ahimou | A61L 2/28 435/31 |
| 2019/0307910 A1 | 10/2019 | Bala | |
| 2021/0353810 A1 * | 11/2021 | Fiorello | A61L 2/28 |
| 2021/0362161 A1 * | 11/2021 | Pan | A61J 1/2093 |

OTHER PUBLICATIONS

Notification of Transmittal of the International Search Report and The Written Opinion of the International Searching Authority, or the Declaration, issued by ISA/EPO in connection with PCT/US2022/041013 on Dec. 2, 2022.
International Preliminary Report on Patentability issued by WIPO on Mar. 7, 2024 in connection with PCT/US2022/041013.

* cited by examiner

*Primary Examiner* — Jennifer Wecker
(74) *Attorney, Agent, or Firm* — Levenfeld Pearlstein, LLC

(57) ABSTRACT

A sterilization challenge device for verifying the efficacy of a gas sterilization process includes an outer container, an inner container, a chemical indicator, and a cap. The outer container includes an open end, a closed end, a chamber configured to contain the inner container containing the chemical indicator, and at least one hole arranged proximate the open end. The cap is configured to engage with the outer container to close the open end, and the at least one hole is configured to provide a flow path for the gaseous sterilant into the chamber.

13 Claims, 4 Drawing Sheets

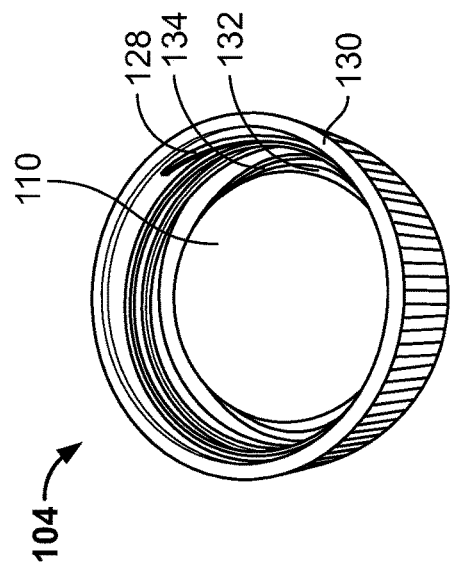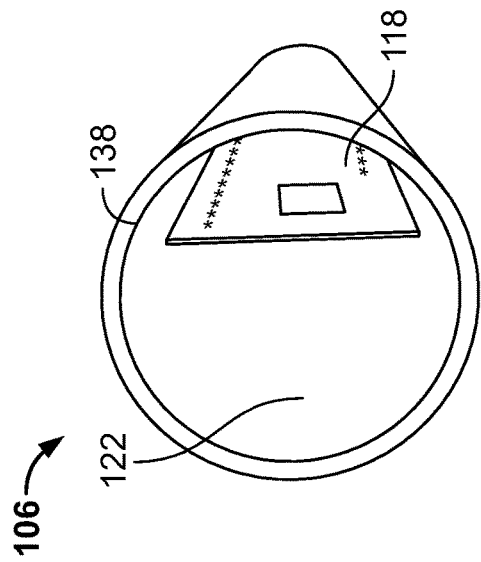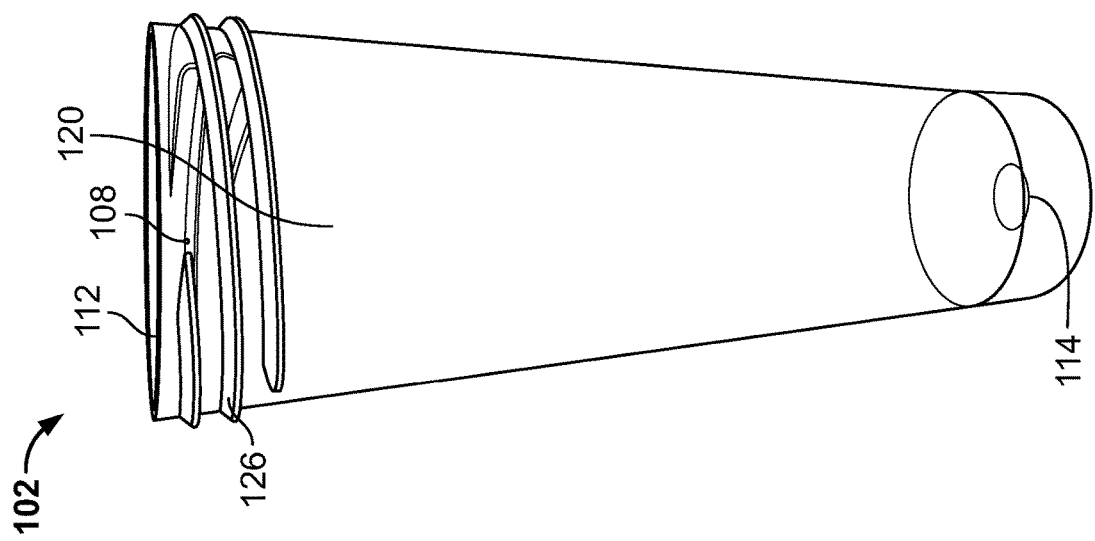

GAS STERILIZATION PROCESS CHALLENGE DEVICE

BACKGROUND

The present invention is directed to a sterilization process challenge device for verifying the efficacy of a sterilization process.

U.S. Pat. No. 9,017,994, which is assigned to the Applicant of the present application and incorporated herein by reference, discloses a sterilization test pack including a biological indicator and a chemical indicator. The sterilization test pack also includes at least one external channel providing a restricted flow path(s) to the biological and chemical indicators, in which the at least one channel is defined by a groove(s) or indentation(s) having a depth, a width, and a length. U.S. Pat. No. 7,790,105, which is also assigned to the Applicant of the present application and incorporated herein by reference, discloses a sterilization challenge specimen holder including a holder configured to hold a sterilization indicator, such as a biological indicator, and a plug including grooves configured to provide a restricted flow path(s) to the sterilization indicator. US Patent Application Publication No. 2019/0307910, which is assigned to the Applicant of the present application and incorporated herein by reference, discloses a sterilization challenge device that includes a filter assembly comprising at least one filter member and at least one gasket, which is configured to restrict flow of steam or gaseous sterilant into a chamber containing a sterilization indicator. U.S. patent application Ser. No. 17/375,086, which is assigned to the Applicant of the present application and incorporated herein by reference, discloses a sterilization challenge device comprising a container and a cap, wherein the container includes a chamber for containing a biological indicator and an insert member and at least one hole defined through a wall of the container to provide a flow path for a gaseous sterilant into the chamber.

An accurate and cost effective verification of sterilization processes is important for obvious reasons. The present disclosure provides an improved sterilization process challenge device for verifying the efficacy of gas sterilization processes.

BRIEF SUMMARY

In one aspect, a sterilization challenge device for verifying the efficacy of a gas sterilization process may comprise an outer container, an inner container, a chemical indicator, and a cap. The outer container may include an outer container wall, an outer container open end, an outer container closed end, an outer container chamber defined therein, and at least one outer container hole defined through a thickness of the outer container wall proximate the outer container open end. The inner container may include an inner container wall, an inner container open end, an inner container closed end, and an inner container chamber defined therein. The cap may be configured to engage with the outer container to close the outer container open end. The chemical indicator may be arranged in the inner container chamber and the at least one outer container wall may be configured to provide a flow path for gaseous sterilant into the outer container chamber when the outer container is closed with the cap.

In an embodiment, the inner container may include an inner container hole defined through a thickness of the inner container. The cap may be provided with a sealing member, wherein the sterilization challenge device may be configured such that the inner container open end is covered by the sealing member and pressed against the sealing member when the outer container is engaged with the cap.

In an embodiment, the cap may include an inner wall, an outer wall, and a ring-shaped space defined therebetween. In such an embodiment, the sterilization challenge device may be configured such that a peripheral portion of the outer container including the at least one outer container hole is received in the ring-shaped space when the outer container is closed with the cap. The flow path for a gaseous sterilant may be defined through a limited space between the outer wall of the cap and the peripheral portion of the outer container, and through the at least one outer container hole.

In an embodiment, the inner container hole may be provided proximate the inner container closed end, and the sealing member may be arranged in a center portion of the cap surrounded by the inner wall. The inner container containing the chemical indicator may be arranged in the outer container chamber, such that the inner container open end faces the cap and the inner container open end is pressed against the sealing member when the outer container is closed with the cap to provide a fluid-tight closure of the inner container open end. In such an embodiment, the flow path may be provided through the at least one outer container hole and through the inner container hole.

In some embodiments, the at least one outer container hole may include a single outer container hole having a diameter of about 0.012 inches to about 0.016 inches, and the inner container hole may have a diameter of about 0.014 inches to about 0.018 inches. For example, the single outer container hole may have a diameter of about 0.014 inches and the inner container hole may have a diameter of about 0.016 inches.

In an embodiment, the outer container chamber may include a cylindrical portion having a constant diameter, and the inner container may include a cylindrical body having an outer diameter less than the constant diameter of the outer container chamber. In such an embodiment, a difference between the constant diameter of the outer container chamber and the outer diameter of the cylindrical body of the inner container may be about 0.125 inches to about 0.25 inches.

In another embodiment, the at least one outer container hole may include a single cut-out provided in a peripheral edge of the outer container open end. The single cut-out may be a radiused cut-out having a depth of about 0.03 inches.

In any of the foregoing embodiments, the outer container may be formed from polypropylene. The inner container may be formed from aluminum. The outer container may include at least one external thread arranged proximate the outer container open end, and the cap may include at least one internal thread arranged along an inner surface of the outer wall and configured to engage the at least one external thread. In an embodiment, the at least one external thread may include double external threads, and the at least one internal thread may include double internal threads configured to engage with the double external threads.

In any of the foregoing embodiments, the sterilization challenge device may be configured such that the chemical indicator may exhibit no color change when a gas sterilization process cycle including three vacuum pulses, each pulse followed by introduction of a gaseous sterilant, is stopped after a half of the cycle, and exhibit a color change when the cycle is completed. The gaseous sterilant may be hydrogen peroxide or ethylene oxide Other aspects, objectives and advantages will become more apparent from the following detailed description.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein:

FIG. 3 is a side perspective view of the outer container of FIG. 1;

FIG. 4 is a top perspective view of the cap of FIG. 1;

FIG. 5 is a top perspective view of the inner container of FIG. 1 with a chemical indicator contained therein;

For simplicity and clarity of illustration, elements shown in the figures may not be drawn to scale. For example, the dimension of some of the elements may be exaggerated relative to each other for clarity.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

It should be further understood that the title of this section of this specification, namely, "Detailed Description", relates to a requirement of the United States Patent Office, and does not imply, nor should be inferred to limit the subject matter disclosed herein.

A sterilization process challenge device according to various embodiments is provided. The challenge device may be configured to verify the efficacy of a hydrogen peroxide gas or ethylene oxide gas sterilization process using a chemical indicator.

Figure 1:
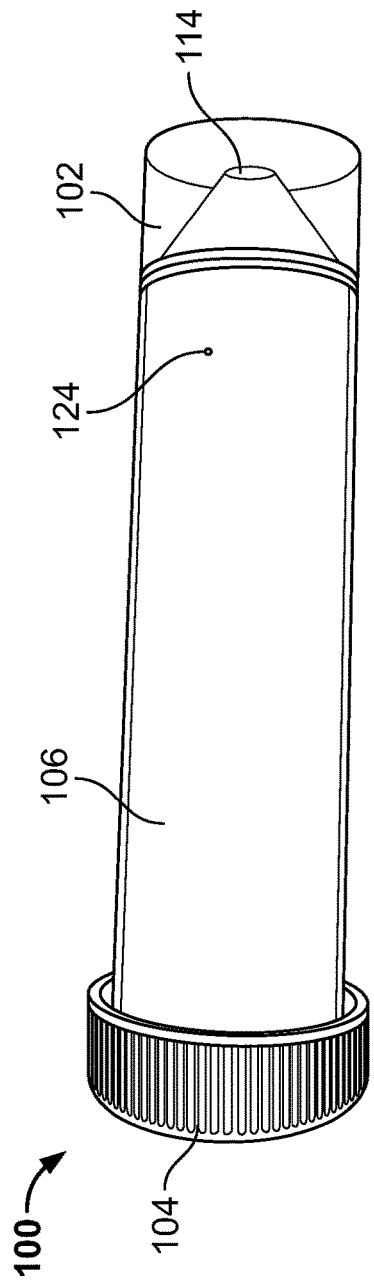
FIG. 1 is a perspective view of a sterilization process challenge device according to an embodiment.
Figure 2:
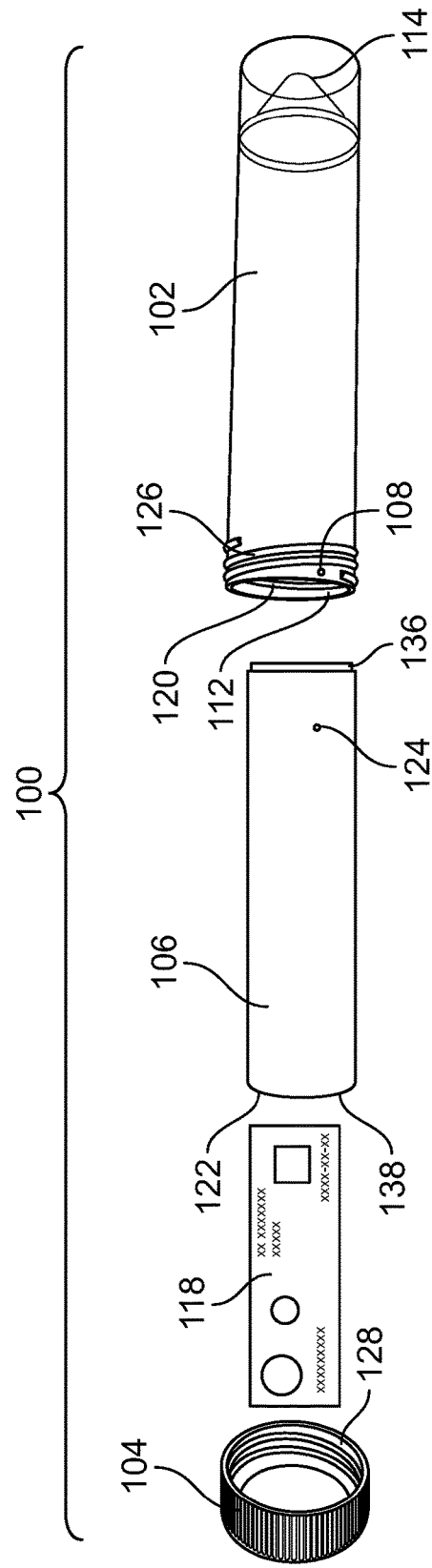
FIG. 2 is an exploded view of the challenge device of FIG. 1.

FIGS. 1 and 2 illustrate a sterilization process challenge device 100 according to an embodiment. FIG. 1 shows the challenge device 100 as assembled and ready for use in a gas sterilization process cycle, and FIG. 2 is an exploded view of the challenge device 100. The challenge device 100 may generally comprise an outer container 102, a cap 104, and an inner container 106. The outer container 102 may have a generally cylindrical shaped body including a chamber 120 defined therein configured to contain the inner container 106. The inner container 106 may have a generally cylindrical shaped body including a chamber 122 defined therein configured to contain a chemical indicator 118. The chemical indicator 118 may include a color change indicator configured to change color to indicate the efficacy of a sterilization process. In other embodiments, the outer container 102 and the inner container 106 may be configured to have a various shaped body, for example, a generally rectangular shaped body.

As best shown in FIGS. 2 and 3, the outer container 102 may include an open end 112, a closed end 114, at least one external thread 126, and at least one hole 108 defined through the thickness of an outer container wall to provide a gas flow path into the chamber 120. The at least one external thread 126 may be provided along an outer surface of the outer container 102 proximate the open end 112 and configured to engage at least one internal thread 128 of the cap 104 (FIGS. 2 and 4) to close the open end 112 of the outer container 102. In an embodiment, the at least one external threads 126 of the outer container 102 may be double threads, and the at least one internal threads 128 of the cap 104 may be the matching double threads configured to engage with the external double threads 126.

The at least one hole 108 may be arranged proximate the open end 112, such that a gas sterilant may flow along the external and internal threads 126, 128 between the outer container 102 and the cap 104 and through the at least one hole 108 to enter the chamber 120 when the outer container 102 is closed with the cap 104. Each of the at least one hole 108 may have a diameter of about 0.01 inches to about 0.02 inches, preferably about 0.012 inches to about 0.018 inches, and more preferably about 0.014 inches to about 0.016 inches. In an embodiment, the at least one hole 108 may include a single hole having a diameter of about 0.014 inches arranged proximate a peripheral edge of the open end 112 as best shown in FIG. 3.

The outer container 102 may be formed from a suitable polymeric material, such as polypropylene, polycarbonate, polyester, polyolefin, polystyrene, polyacrylamide, polymethacrylate, poly(methyl)methacrylate, polyimide, polyethylene terephthalate, polybutylene terephthalate, polyvinylchloride, and other similar polymers, or a metallic material such as aluminum. In an embodiment, the outer container 102 may be formed from polypropylene and may have a wall thickness of about 1/16 inches.

The cap 104 may include an outer wall 130, an inner wall 132, a sealing member 110 arranged in a generally circular space defined in the inner wall 132, and the at least one internal thread 128 formed along an inner surface of the outer wall 130 as best shown in FIG. 4. The inner wall 132 may be configured to fit in the open end 112 of the outer container 102, such that a peripheral portion of the outer container 102 proximate the open end 112 may be received in a ring-shaped space 134 defined between the outer wall 130 and inner wall 132.

In this embodiment, the sealing member 110 having a generally circular shaped body may be arranged in a center portion of the cap 104 surrounded by the inner wall 132. The sealing member 110 may be formed from a suitable sealing material, such as an elastomer or rubber. The cap 104 may be formed from a suitable polymeric material, such as polyethylene, polypropylene, polyester, or other similar polymers. In an embodiment, the cap 104 may be formed from polyethylene. The challenge device 100 may be configured such that a gas flow path into the chamber 120 may be provided along the external and internal threads 126, 128 between the outer container 102 and the cap 104 and through the at least one hole 108 when the outer container 102 is closed with the cap 104.

The inner container 106 may include the chamber 122 defined in a generally cylindrical shaped body, a closed end 136, an open end 138, and a hole 124 defined through the thickness of an inner container wall proximate the closed end 136 and configured to provide a gas flow path into the chamber 122. In an embodiment, the inner container 106 may be configured such that when the inner container 106 is placed in the chamber 120 of the outer container 102 and the outer container 102 is closed with the cap 104, the open end 138 of the inner container 106 may be pressed against the sealing member 110 and closed fluid-tight. In such an embodiment, a gas flow path into the inner container chamber 122 may be provided along the external and internal threads 126, 128 between the outer container 102 and the cap 104, and through the at least one hole 108 provided in the outer container 102, and through the hole 124 provided in the inner container 106.

The hole 124 may have a diameter of about 0.01 inches to about 0.02 inches, preferably about 0.014 inches to about 0.018 inches. In an embodiment, the hole 124 may have a diameter of about 0.016 inches and provided in a lower portion of the inner container 106 proximate the closed end 136 as shown in FIGS. 1 and 2. The inner container 106 may be formed from a suitable material, such as aluminum, metal, or polymeric materials. In an embodiment, the inner container 106 may be formed from aluminum and have a wall thickness of about 1/16 inches.

To prepare the challenge device 100, the chemical indicator 118 may be placed in the inner container chamber 122, and the inner container 106 including the chemical indicator 118 may be placed in the outer container chamber 120, such that the open end 138 of the inner container 106 may be arranged adjacent the cap 104 when the outer container 102 is closed with the cap 104. The open end 138 may have a smaller diameter than the sealing member 110, such that the open end 138 may be pressed against the sealing member 110 to create a fluid-tight seal between the inner container 106 and the cap 104 when the outer container 102 is closed with the cap 104.

In an embodiment, the outer container 108 may have a generally cylindrical body with a tapering closed end portion to provide the chamber 120 including an upper portion having a generally constant diameter and a closed end portion having a gradually decreasing diameter to form a conical-shaped closed end portion 136 as shown in FIGS. 1 and 2. In such an embodiment, the inner container 106 having an outer diameter smaller than a diameter of the upper portion of the outer container chamber 120 may sit in the conical-shaped closed end portion 136, such that the inner container 106 may be generally centered in the outer container chamber 120 to allow the open end 138 of the inner container 106 to be completely covered and sealingly closed by the sealing member 110 when the outer container 102 is closed with the cap 104. In an embodiment, a diameter of the upper portion of the outer container chamber 120 may be greater than an outer diameter of the inner container 106 by about 0.125 inches to 0.25 inches. For example, the upper portion of the outer container chamber 120 may have a diameter of about 1.125 inches, while the inner container 106 may have an outer diameter of about 1 inch.

The challenge device 100 may be configured to increase a flow restriction of a gaseous sterilant, such as hydrogen peroxide gas or ethylene oxide gas, into the inner container chamber 122 to reach the chemical indicator 118. In an embodiment, the challenge device 100 may be configured such that a gaseous sterilant may flow along the external and internal threads 126, 128 between the outer container 102 and the cap 104, and through the single hole 108 provided proximate the open end 112 of the outer container 102, and through the outer container chamber 120 between the inner container 106 and the outer container 102, and through the hole 124 provided proximate the closed end 136 of the inner container 106 to reach the chemical indicator 118.

In an embodiment the outer container 102 may have an inner diameter of about 0.75 inches to about 1.5 inches, preferably about 0.875 inches to about 1.25 inches, and a length of the chamber portion having a constant diameter of about 4 inches to about 6 inches, preferably about 4.5 inches to about 5.5 inches. The inner container 106 may have an outer diameter of about 0.5 inches to about 1.375 inches, preferably about 0.625 inches to about 1.125 inches, and a height of about 3.75 inches to about 5.875 inches, preferably about 4.25 inches to about 5.375 inches. In such an embodiment, the challenge device 100 may be configured such that a difference between the inner diameter of the outer container 102 in the chamber portion having a constant diameter and the outer diameter of the inner container 106 may be about 0.125 inches to about 0.25 inches and a clearance between the outer container open end 112 and the inner container open end 138 may be about 0.125 inches to about 0.25 inches.

Figure 6:
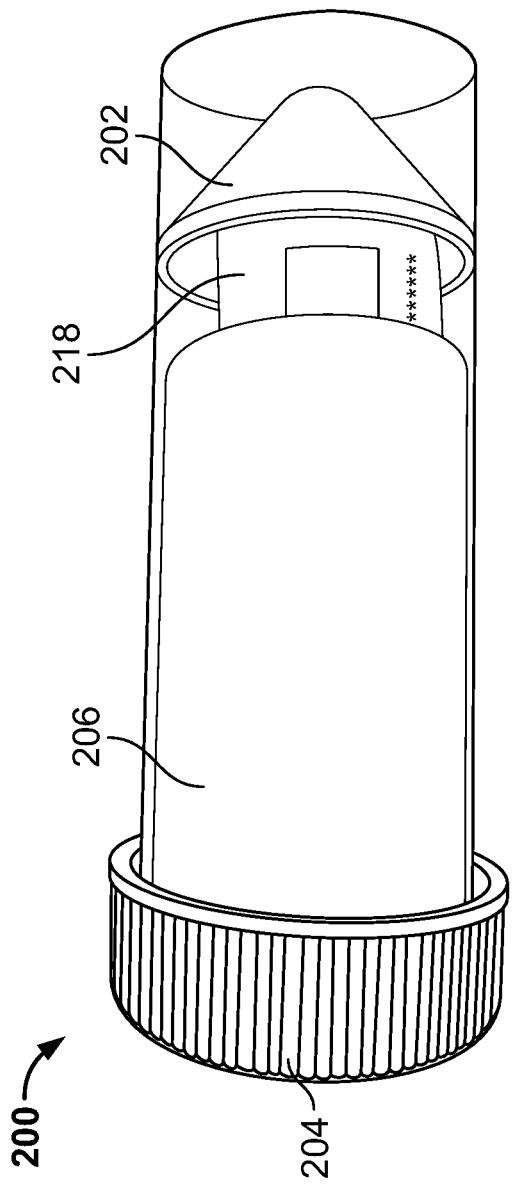
FIG. 6 is a perspective view of a sterilization process challenge device according to another embodiment.
Figure 7:
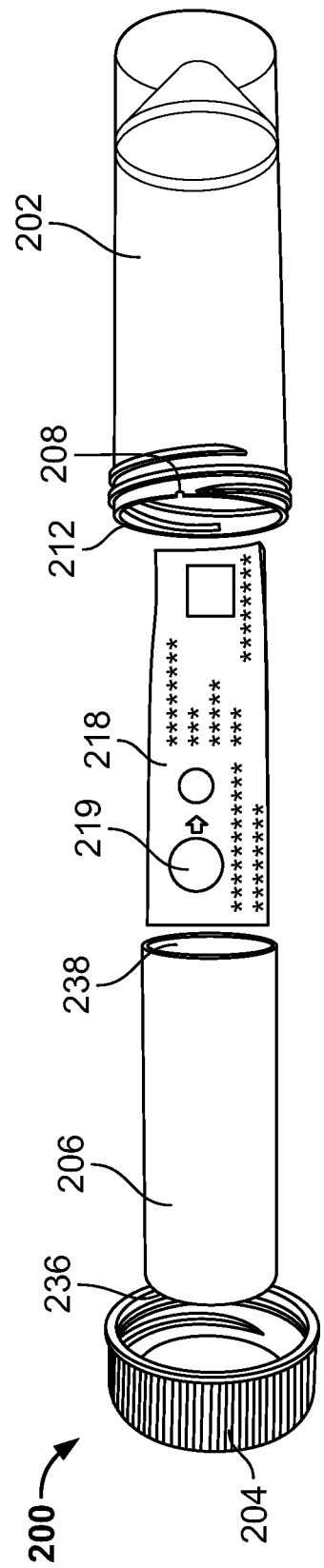
FIG. 7 is an exploded view of the challenge device of FIG. 6.

FIGS. 6 and 7 show a sterilization process challenge device 200 according to another embodiment. The challenge device 200 may be configured similar to the challenge device 100 generally comprising an outer container 202, a cap 204, an inner container 206, and a chemical indicator 218. In this embodiment, the outer container 202 may be provided with at least one cut-out 208 in a peripheral edge of an open end 212.

Figure 8:
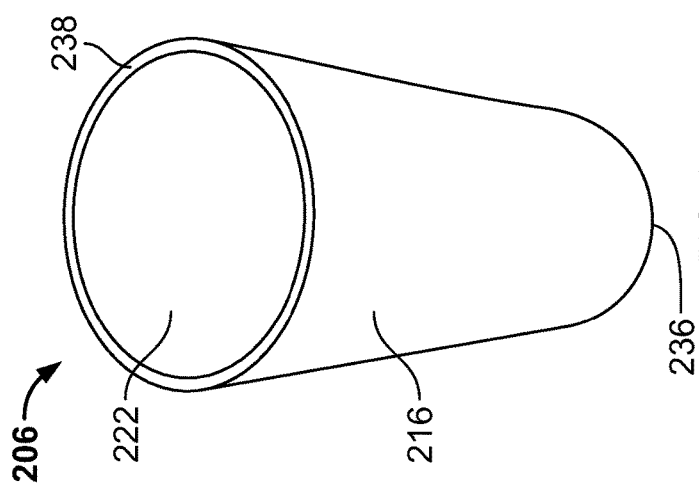
FIG. 8 is a top side perspective view of the inner container of FIG. 6.

The inner container 206 may include a generally cylindrical shaped body 216 having a closed end 236, an open end 238, and a chamber 222 defined therein, which may be configured to contain at least a portion of the chemical indicator 218 as shown in FIGS. 6-8. The chemical indicator 218 may include a color change indicator 219 configured to change color to indicate the efficacy of a sterilization process.

Figure 10:
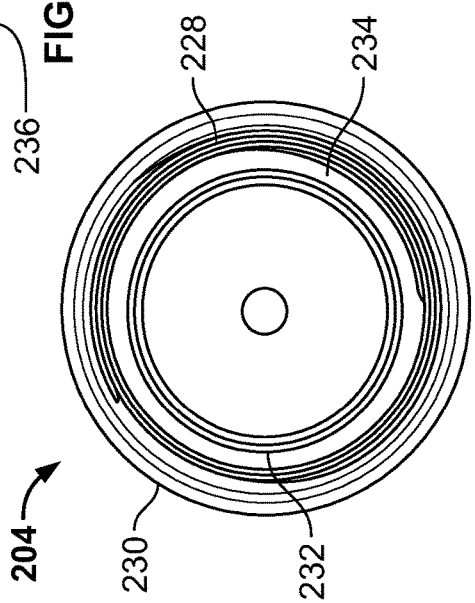
FIG. 10 is a top perspective view of the cap of FIG. 6.

The cap 204 may be configured similar to the cap 104 including an outer wall 230, an inner wall 232, and an internal thread 228 as shown in FIG. 10. As it was with the challenge device 100, the challenge device 200 may be configured such that a peripheral portion of the outer container 202 proximate the open end 212 may be received in a ring-shaped space 234 defined between the outer wall 230 and inner wall 232 of the cap 204 when the outer container 202 is closed with the cap 204. In this embodiment, the cap 204 may not include a sealing member. In other embodiments, the cap 204 may include a sealing member similar to the sealing member 110.

Figure 9:
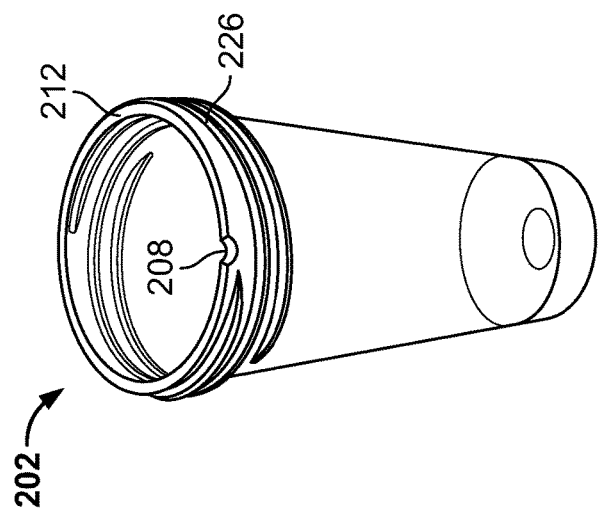
FIG. 9 is a top side perspective view of the outer container of FIG. 6.

The outer container 202 may include an external thread 226 and at least one cut-out 208 provided in a peripheral portion configured to be received in the ring-shaped space 234 of the cap 204. In this embodiment, the outer container 202 may include a single cut-out 208 provided in a peripheral edge portion defining the open end 212 as shown in FIGS. 7 and 9. In an embodiment, the cut-out 210 may be formed using a 1/8-3/8 inches end mill to provide a radiused cut-out having a depth of about 0.015 inches to about 0.05 inches, for example, about 0.03 inches. A restrictive flow path for a gaseous sterilant may be provided along the external and internal threads 226, 228 between the outer wall 230 of the cap 204 and the peripheral portion of the outer container 202, and through the at least one cut-out 208.

Figure 11:
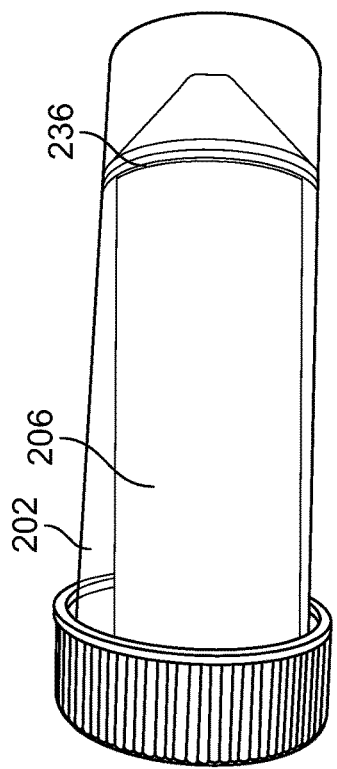
FIG. 11 is a perspective view of a sterilization process challenge device according to yet another embodiment.

In FIG. 6, the inner container 206 with the chemical indicator 218 received therein is placed in the outer container 202 with the closed end 236 of the inner container 206 facing the open end 212 of the outer container 202. In other embodiments, the inner container 206 with the chemical indicator 218 received therein may be arranged in the outer container 202 with the open end 238 of the inner container 206 facing the open end 212 of the outer container 202 as shown in FIG. 11. In some embodiments, the inner container 206 may be configured to contain the chemical indicator 218 entirely within the chamber 222.

In use, the challenge device 100, 200 may be placed in a sterilization chamber along with objects to be sterilized. A sterilization process may include at least one vacuum phase to remove air from the sterilization chamber followed by introduction of a gaseous sterilant. In an embodiment, a sterilization process includes three vacuum pulses, each pulse followed by introduction of a gaseous sterilant. In such a sterilization process, air in the challenge device 100, 200 may be removed during the vacuum pulses and the gaseous sterilant may flow into the challenge device 100, 200 through the gas flow path described in the foregoing embodiments.

Samples of the sterilization process challenge device 100 were prepared and tested in a sterilization process cycle using a hydrogen peroxide gas. Each of the samples comprised an outer container 102 formed from polypropylene and having an inner diameter of about 1.125 inches and a length of a chamber portion having a constant diameter of about 4 inches. The outer container 102 also included double external threads 126 and a single hole 108 having a diameter of about 0.014 inches arranged proximate the open end 112. A cap 104 formed from polyethylene included a sealing member 110 and double internal threads 128 configured to engage with the double external threads 126 of the outer container 102. An inner container 106 formed from aluminum had an outer diameter of about 1 inch and a length of about 3.875 inches and included a single hole 124 having a diameter of about 0.016 inches provided proximate a closed end 136 of the inner container 106. The challenge device samples were prepared by inserting a chemical indicator 118 in the inner container 106, placing the inner container 106 containing the chemical indicator 118 in the outer container 102 with the open end 138 of the inner container 106 facing the open end 112 of the outer container 102, and closing the outer container 102 with the cap 104 such that the open end 138 of the inner container 106 is pressed against the sealing member 110.

A set of challenge device samples were tested in the sterilization process cycles, wherein the sterilization process cycles were stopped after a ½ cycle and the chemical indicators 118 were examined. Each of the chemical indicator 118 of the challenge device samples exhibited a no color change indicating that the challenge device samples restricted a flow of hydrogen peroxide into the inner container chamber 122. Further, another set of challenge device samples were tested in the sterilization process cycles, wherein the chemical indicators 118 were examined after the sterilization cycles were completed. Each of the chemical indicators 118 of the challenge device samples exhibited a color change indicating that hydrogen peroxide has reached the inner container chamber 122.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A sterilization challenge device for verifying an efficacy of a gas sterilization process, comprising:
    an outer container including an outer container wall, an outer container open end, an outer container closed end, an outer container chamber defined therein, and at least one outer container hole defined through a thickness of the outer container wall proximate the outer container open end, the outer container having an external thread proximate the open end;
    an inner container including an inner container wall, an inner container open end, an inner container closed end, and an inner container chamber defined therein;
    a chemical indicator arranged in the inner container chamber; and
    a cap configured to engage with the outer container to close the outer container open end, the cap including an internal thread arranged along an inner surface of the outer wall and configured to engage the outer container external thread,
    wherein the outer chamber is configured to contain the inner container and the chemical indicator arranged therein, wherein the at least one outer container hole is configured to provide a flow path for a gaseous sterilant into the outer container chamber,
    wherein the at least one outer container hole is disposed between the thread and the open end, and
    wherein the inner container includes an inner container hole defined through a thickness of the inner container wall, and the cap includes a sealing member, wherein the sterilization challenge device is configured such that the inner container open end is covered by the sealing member and pressed against the sealing member when the outer container is engaged with the cap.

2. The sterilization challenge device of claim 1, wherein the cap includes an inner wall, an outer wall, and a ring-shaped space defined therebetween, wherein sterilization challenge device is configured such that a peripheral portion including the at least one outer container hole is received in the ring-shaped space when the outer container is closed with the cap, and wherein the flow path for a gaseous sterilant is provided through a limited space defined between the outer wall of the cap and the peripheral portion of the outer container and through the at least one outer container hole.

3. The sterilization challenge device of claim 1, wherein the inner container hole is provided proximate the inner container closed end and the sealing member is arranged in a center portion of the cap surrounded by the inner wall, wherein the inner container containing the chemical indicator is arranged in the outer container chamber such that the inner container open end faces the cap and the inner container open end is pressed against the sealing member when the outer container is closed with the cap to provide a fluid-tight closure of the inner container open end, wherein the flow path is provided through the at least one outer container hole and through the inner container hole.

4. The sterilization challenge device of claim 3, wherein the at least one outer container hole includes a single outer container hole having a diameter of about 0.012 inches to about 0.016 inches, and the inner container hole has a diameter of about 0.014 inches to about 0.018 inches.

5. The sterilization challenge device of claim 4, wherein the single outer container hole has a diameter of about 0.014 inches and the inner container hole has a diameter of about 0.016 inches.

6. The sterilization challenge device of claim 1, wherein the outer container chamber includes a cylindrical portion having a constant diameter, and the inner container includes a cylindrical body having an outer diameter less than the constant diameter of the outer container chamber, wherein a difference between the constant diameter of the outer container chamber and the outer diameter of the cylindrical body of the inner container is about 0.125 inches to about 0.25 inches.

7. The sterilization challenge device of claim 1, wherein the at least one outer container hole includes a single cut-out provided in a peripheral edge of the outer container open end.

8. The sterilization challenge device of claim 7, wherein the single cut-out is a radiused cut-out having a depth of about 0.03 inches.

9. The sterilization challenge device of claim 1, wherein the outer container is formed from polypropylene.

10. The sterilization challenge device of claim 1, wherein the inner container is formed from aluminum.

11. The sterilization challenge device of claim 1, wherein the outer container external thread includes double external threads, and the cap internal thread includes double internal threads configured to engage with the double external threads.

12. The sterilization challenge device of claim 1, wherein the gaseous sterilant is hydrogen peroxide or ethylene oxide.

13. The sterilization challenge device of claim 1, wherein the sterilization challenge device is configured such that the chemical indicator exhibits no color change when a gas sterilization process cycle including three vacuum pulses, each pulse followed by introduction of a gaseous sterilant, is stopped after a half of the cycle, and exhibits a color change when the cycle is completed.

* * * * *